(12) United States Patent
Gohara et al.

(10) Patent No.: US 8,994,811 B2
(45) Date of Patent: Mar. 31, 2015

(54) DIFFRACTION MICROSCOPY (75) Inventors: Kazutoshi Gohara, Hokkaido (JP); Kota Kawahara, Hokkaido (JP)

(73) Assignee: National University Corporation Hokkaido University, Hokkaido (JP)

( * ) Notice: Subject to any disclaimer, the term of this patent is extended or adjusted under 35 U.S.C. 154(b) by 437 days.

(21) Appl. No.: 13/575,776

(22) PCT Filed: Jan. 21, 2011

(86) PCT No.: PCT/JP2011/000318
§ 371 (c)(1),
(2), (4) Date: Jul. 27, 2012

(87) PCT Pub. No.: WO2011/093043
PCT Pub. Date: Aug. 4, 2011

(65) Prior Publication Data
US 2012/0320185 A1 Dec. 20, 2012

(30) Foreign Application Priority Data
Jan. 27, 2010 (JP) .................. 2010-015698

(51) Int. Cl.
*H04N 9/47* (2006.01)
*H04N 7/18* (2006.01)
*G02B 21/36* (2006.01)
*G01N 23/20* (2006.01)
(Continued)

(52) U.S. Cl.
CPC ........ *G02B 21/365* (2013.01); *G01N 23/20058* (2013.01); *G02B 26/0808* (2013.01); *G02B 27/4205* (2013.01); *H01J 37/222* (2013.01); *H01J 37/244* (2013.01); *H01J 37/295* (2013.01); *H01J 2237/223* (2013.01); *H01J 2237/226* (2013.01)

USPC .................. 348/79; 348/68; 348/94; 348/180; 348/774; 359/207.1; 359/217.1; 359/217.4; 359/204.2; 359/204.3; 359/204.4; 359/204.5; 359/196.1; 359/211.6; 359/558; 359/559; 359/560; 359/563

(58) Field of Classification Search
USPC ............ 348/79, 68, 94, 180, 774; 359/207.1, 359/217.4, 204.2, 204.3, 204.4, 204.5, 359/196.1, 211.6, 558, 559, 560, 563
See application file for complete search history.

(56) References Cited

U.S. PATENT DOCUMENTS 5,800,950 A * 9/1998 Hirao et al. ................ 430/1
7,847,238 B2 * 12/2010 Grier ......................... 250/251
(Continued)

OTHER PUBLICATIONS

J. C. H. Spence, Science of Microscopy (eds P. W. Hawkes and J. C. H. Spence), Springer, New York, 2007.
(Continued)

*Primary Examiner* — Jefferey Harold
*Assistant Examiner* — Mustafizur Rahman
(74) *Attorney, Agent, or Firm* — Brundidge & Stanger, P.C.

(57) ABSTRACT

Disclosed is a diffraction microscopy capable of reducing influence of an increase in the incident angle range of a beam. Specifically disclosed is a diffraction microscopy in which a beam is incident on a sample, in which the intensity of a diffraction pattern from the sample is measured, and in which an image of an object is rebuilt using Fourier interactive phase retrieval on the basis of the measured intensity of the diffraction pattern. In this method, Fourier interactive phase retrieval is performed using deconvolution on the diffraction pattern subjected to convolution by the increase in the incident angle range of the beam.

2 Claims, 8 Drawing Sheets (51) Int. Cl.
  *G02B 26/08* (2006.01)
  *G02B 27/42* (2006.01)
  *H01J 37/22* (2006.01)
  *H01J 37/244* (2006.01)
  *H01J 37/295* (2006.01)

(56) References Cited

U.S. PATENT DOCUMENTS

2009/0169636 A1* 7/2009 O' Hagan et al. ............. 424/499
2011/0038900 A1* 2/2011 Chakrapani et al. .......... 424/400
2011/0280949 A1* 11/2011 Malyala et al. ............... 424/501
2012/0263753 A1* 10/2012 O'Hagan et al. ........... 424/204.1

OTHER PUBLICATIONS

Kazutoshi Gohara et al., Electron Diffractive Imaging, Kenbikyo, Mar. 30, 2009, vol. 44, No. 1, pp. 69 to 73.
O. Kamimura, K. Kawahara, T. Doi, T. Dobashi, T. Abe, and K. Gohara: Diffraction microscopy using 20 kV electron beam for multiwall carbon nanotubes, Appl. Phys. Lett., 92, 024106(1-3), 2008.
O. Kamimura, T. Dobashi, K. Kawahara, T. Abe, and K. Gohara: 10-kV diffractive imaging using newly developed electron diffraction microscope, Ultramicroscopy, in press (On line: doi:10.1016/j.ultramic.2009.10010, 2010. 12.
R. W. Gerchberg, Nature, 240, 404-406, 1972.
J. R. Fienup, Appl. Opt., 21(15), 2758-2769, 1982.
J. Miao, P. Charalambous, J. Kirz and D. Sayre: Nature, 400, 342-344, 1999.
I. A. Vartanyants and I. K. Robinson, J. Phys.: Condens. Matter 13, 10593, 2001.
U. Weierstall, Q. Chen, J. C. H. Spence, M. R. Howells, M. Isaacson, and R. R. Panepucci, Ultramicroscopy 90, 171, 2002.
P. Jansson, Deconvolution of images and spectra (Academic Press, 1997).
K. Kawahara, K. Gohara, H. Shioya, Beam-divergence deconvolution for Fourier interative phase retrieval method, IEICE Technicla Report, Jan. 18, 2007, vol. 106, No. 500, pp. 25 to 29.
K. Gohara, K. Kawahara, O. Kaminura, H. Shioya, Electron Diffractive Imaging, Abstracts of the Meeting of the Physical Society of Japan, Aug. 21, 2007, vol. 62, No. 2, p. 991.
Argument regarding amendment under PCT article 34 for PCT/JP2011/000318, submitted on Mar. 15, 2011.

* cited by examiner

DIFFRACTION MICROSCOPY

TECHNICAL FIELD

The present invention relates to diffraction microscopy that performs imaging by digital processing of a computer based on a diffraction pattern obtained by experiment.

BACKGROUND ART

How significant it is to know a structure of a substance at a spatial resolution as high as an atom can be identified, is obvious from atomic scale structure elucidations of DNA, carbon nanotube, and the like as well as subsequent developments. A diffraction pattern of X-rays or electron beams has an important role in the structure elucidations. In fields dealing with structures of atomic scale, it has been a general common sense that a phenomenon of diffraction has relevance only to crystals having periodicity. However, the common sense is greatly changing as a result of emergence of a new method called "diffraction microscopy" or "diffractive imaging". See NPL 1.

Figure 1A:
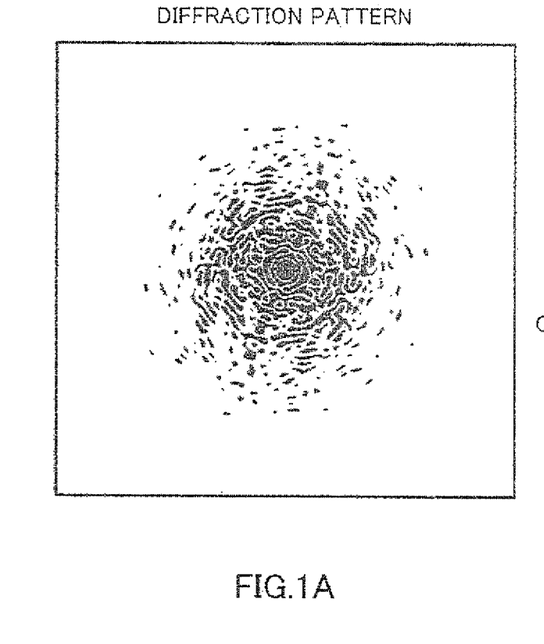
FIG. 1 is a diagram showing an example for describing diffraction microscopy.
Figure 1B:
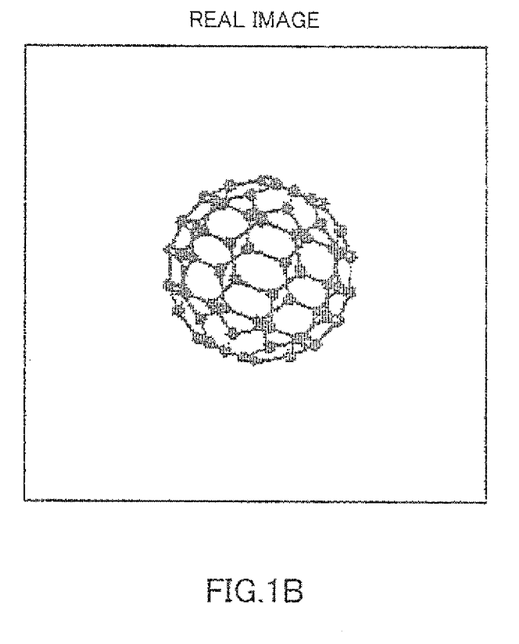

As shown in FIG. 1, the diffraction microscopy is an imaging method for obtaining a real image by numerical calculation using a computer based on a diffraction pattern measured by experiment, and the diffraction microscopy can be referred to as a "digital lens" that realizes a function of a physical lens by digital calculation. The diffraction microscopy does not require a lens for image formation, and in principle, imaging at diffraction limit resolution can also be realized for a non-crystalline substance without periodicity, although the diffraction microscopy is based on the diffraction pattern. The diffraction microscopy can be generally applied to any substance with the wavy nature and can be applied to electrons with de Broglie wavelength. In recent years, the diffraction microscopy has significantly drawn attention, and advanced studies are globally progressed. See NPLs 2 to 4.

Basics of the diffraction microscopy are provided by NPLs 5 and 6.

Figure 2:
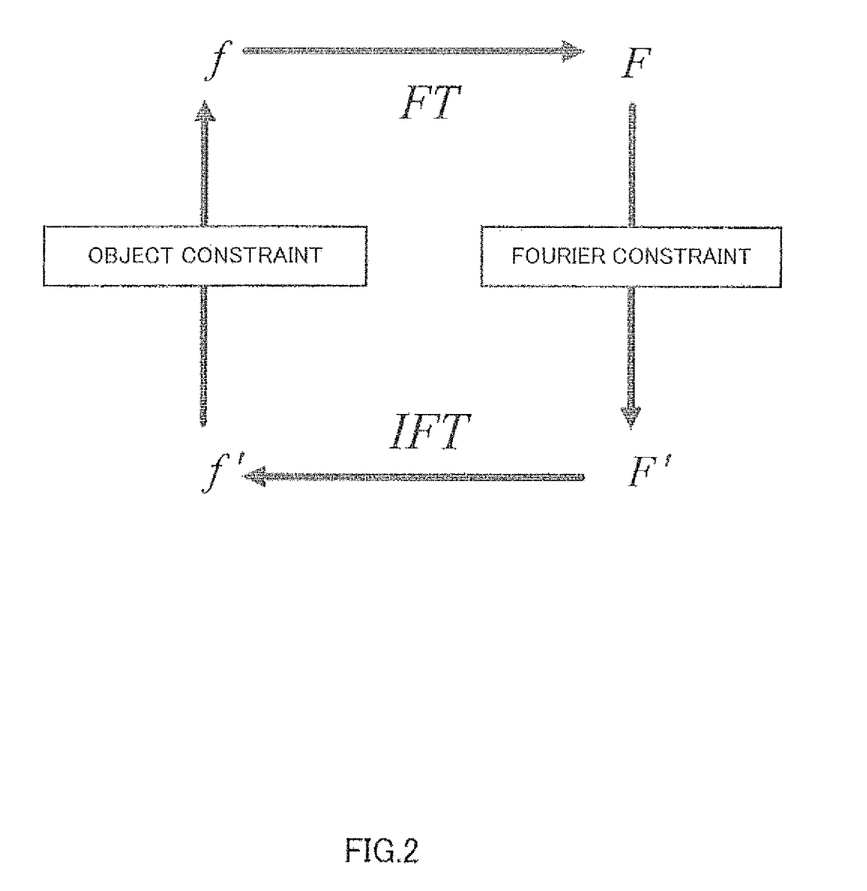
FIG. 2 is a diagram showing a basic principle (algorithm) of Fourier iterative phase retrieval as a basis of the diffraction microscopy.

FIG. 2 is a diagram showing a basic algorithm of the diffraction microscopy. In FIG. 2, f denotes an object, and F denotes what is obtained by applying Fourier transform FT{f} to object f. In FIG. 2, f and F are complex functions and corresponding amplitudes and phases are |f| and |F| as well as $\phi$ and $\Phi$, respectively. The physical quantity generally obtained by diffraction experiment is only the diffraction intensity, i.e. amplitude, and the phase cannot be obtained. If the phase could be obtained by any kind of method, the object can be obtained by inverse Fourier transform. Therefore, "Fourier iterative phase retrieval" for obtaining the phase is proposed in NPLs 5 and 6. As shown in FIG. 2, the Fourier iterative phase retrieval is a method of applying respective constraints both in a real space and a reciprocal space (frequency area), i.e. "object constraint" and "Fourier constraint" (amplitude obtained by diffraction experiment), and sequentially and alternately repeating the Fourier transform and the inverse Fourier transform to obtain the phase. It is experimentally verified in NPL 7 that this method can provide an image of the object. The method of providing the object constraint varies depending on a specific algorithm.

FIG. 1 shows an example of simulation of the diffraction microscopy. The diffraction pattern on the left side is used as the Fourier constraint, and the object constraints are a real function, non-negativity and setting an area (support) surrounding a target to zero. An update algorithm called HIO (Hybrid Input-Output) is applied up to 5000 iterations, and an update algorithm called ER (Error Reduction) is applied after that and up to 10000 iterations. In this way, the real image on the right side is obtained. Although the diffraction pattern is created based on the real image because this is a simulation, the original real image is accurately reconfigured.

CITATION LIST

Non-Patent Literature

NPL 1
J. C. H. Spence, *Science of Microscopy* (eds P. W. Hawkes and J. C. H. Spence), Springer, New York, 2007.
NPL 2
Kazutoshi Gohara and Osamu Kamimura: Microscope, 44(1), 69-73, 2009.
NPL 3
O. Kamimura, K. Kawahara, T. Doi, T. Dobashi, T. Abe, and K. Gohara: Diffraction microscopy using 20 kV electron beam for multiwall carbon nanotubes, Appl. Phys. Lett., 92, 024106(1-3), 2008.
NPL 4
O. Kamimura, T. Dobashi, K. Kawahara, T. Abe, and K. Gohara: 10-kV diffractive imaging using newly developed electron diffraction microscope, Ultramicroscopy, in press (On line: doi:10.1016/j.ultramic.2009.10010, 2010.12.
NPL 5
R. W. Gerchberg, *Nature*, 404-406, 1972.
NPL 6
J. R. Fienup, *Appl. Opt.*, 21(15), 2758-2769, 1982.
NPL 7
J. Miao, P. Charalambous, J. Kirz and D. Sayre: *Nature*, 400, 342-344, 1999.
NPL 8
I. A. Vartanyants and I. K. Robinson, J. Phys.: Condens. Matter 13, 10593, 2001.
NPL 9
U. Weierstall, Q. Chen, J. C. H. Spence, M. R. Howells, M. Isaacson, and R. R. Panepucci, Ultramicroscopy 90, 171, 2002.
NPL 10
P. Jansson, Deconvolution of images and spectra (Academic Press, 1997).

SUMMARY OF INVENTION

Technical Problem

Figure 3:
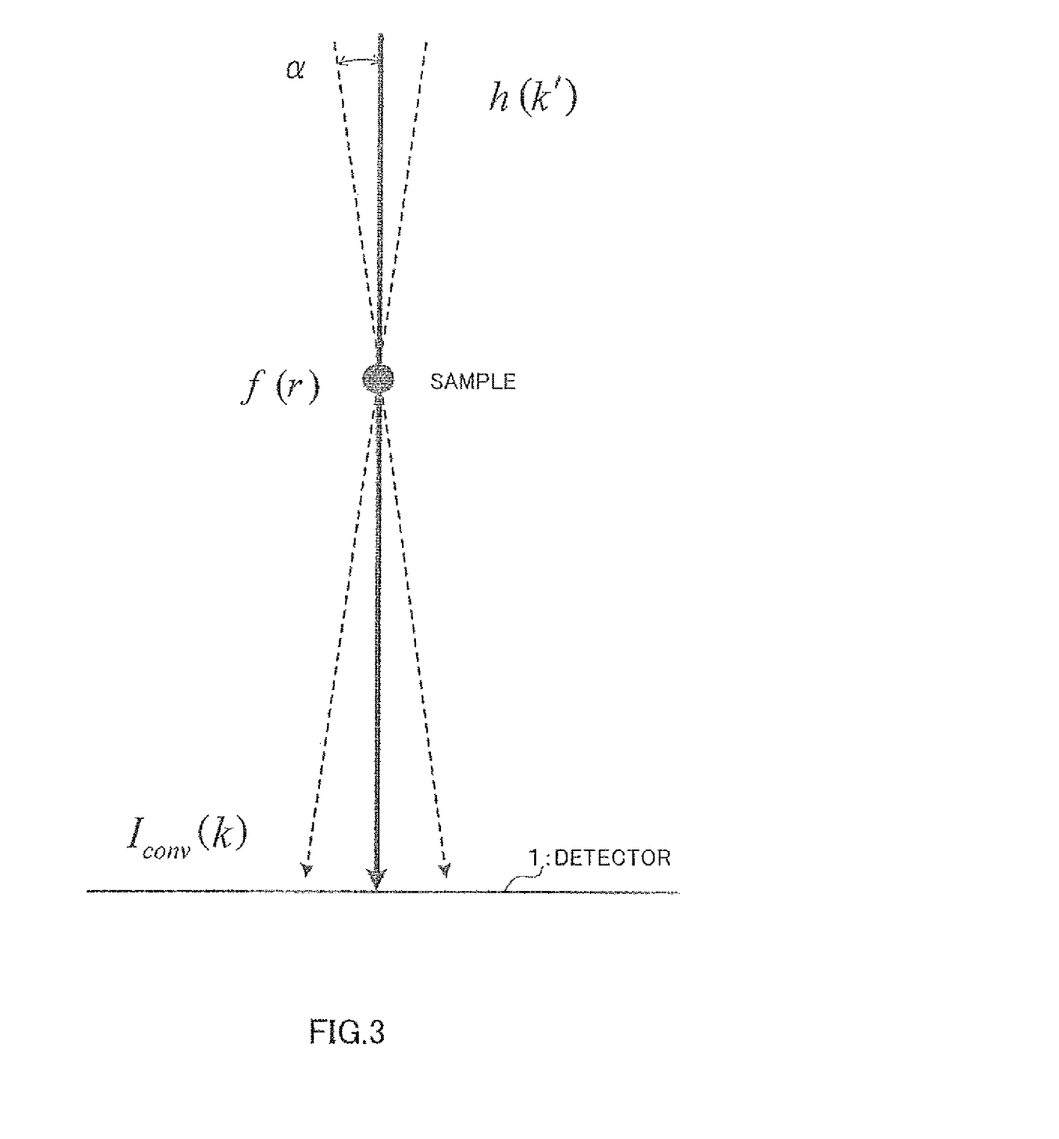
FIG. 3 is a diagram for describing an angle spread of incident beam.

One of the problems in the diffraction microscopy is an angle spread of incident beam. The "angle spread of incident beam" denotes, as shown in FIG. 3, that a wave enters an imaging target object at different angles. NPLs 8 and 9 have already pointed out that the angle spread of incident beam is one of the important problems in the diffraction microscopy. However, a method of solving the problem is not proposed in these literatures. The problem of the angle spread of incident beam will be described in detail later.

An object of the present invention is to provide diffraction microscopy that can reduce influence of an angle spread of incident beam.

Solution to Problem

To achieve the object, diffraction microscopy reflecting one aspect of the present invention radiates a beam on a sample, measures intensity of a diffraction pattern from the sample, and uses Fourier iterative phase retrieval based on the measured intensity of the diffraction pattern to reconfigure an image of an object, wherein deconvolution is used to apply the Fourier iterative phase retrieval to a diffraction pattern convoluted by an angle spread of incident beam.

Advantageous Effects of Invention

According to the present invention, the influence of the angle spread of incident beam can be reduced in the diffraction microscopy.

DESCRIPTION OF EMBODIMENTS

Hereinafter, an embodiment of the present invention will be described in detail with reference to the drawings.

First, an angle spread of incident beam will be described with reference to FIG. 3.

When a wave is scattered only once by object f(r) (first Born approximation) and the scattered wave is observed at a great distance (Fraunhofer diffraction), diffraction intensity $I_0(k)$ by a parallel incident beam measured at point k of detector 1 (detection surface) is proportional to the square of amplitude of Fourier transform $F(k)=FT\{f(r)\}$ of object f(r). Therefore, assuming that a proportionality coefficient is 1 for the simplification, formula (1) is established.

[Expression 1]

$$I_0(k)=|F(k)|^2=|FT\{f(r)\}|^2 \qquad (1)$$

When there is an angle spread in the incident beam, diffraction pattern intensity $I_{conv}(k)$ measured by experiment at point k of the detection surface is expressed by formula (2) as a convolution of diffraction intensity $I_0(k)$ by the parallel incident beam and angle spread intensity distribution h(k) of the incident beam.

[Expression 2]

$$I_{conv}(k)=\int_{-\infty}^{\infty} I_0(k-k')h(k')dk' \qquad (2)$$

In the actual experiment, quantum noise is superimposed on the diffraction pattern intensity measured by detector 1. The quantum noise is expressed by Poisson distribution P(n; ρ), where ρ is an expected value. Poisson distribution P(n;ρ) is provided by formula (3). Here, n denotes intensity when there is noise in the points, and expected value ρ denotes intensity when there is no noise in the points.

[Expression 3]

$$P(n;\rho) = \frac{\rho^n e^{-\rho}}{n!} \qquad (3)$$

The formulas allow simulation of influence on the diffraction microscopy when the quantum noise is superimposed on the angle spread of the incident beam.

Figure 4A:
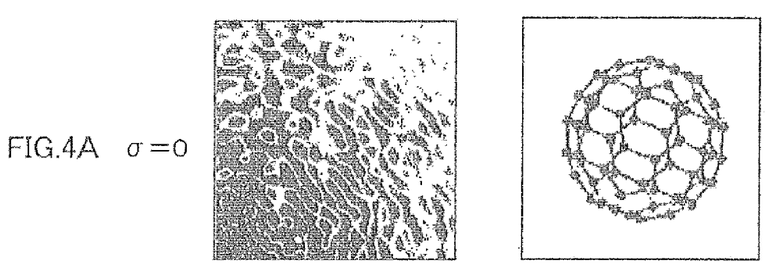
FIG. 4 is a diagram for describing influence of the angle spread of incident beam.
Figure 4B:
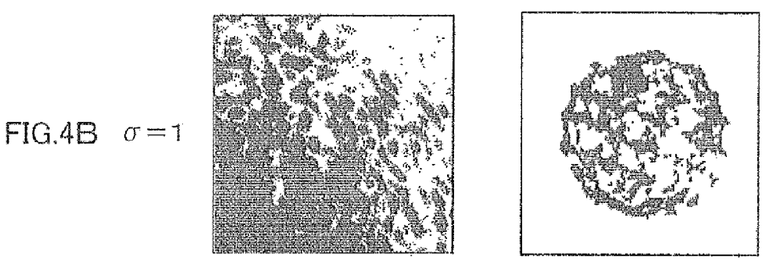
Figure 4C:
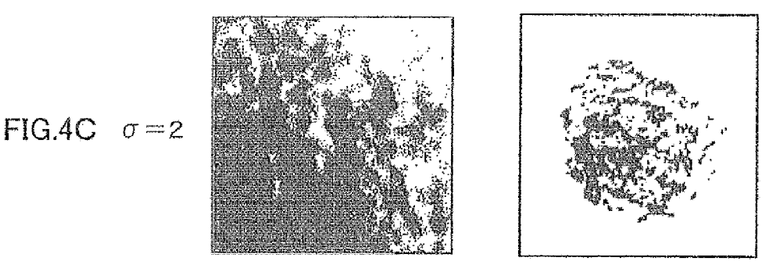

FIG. 4 is a diagram showing an example of the influence of the angle spread of incident beam. Angle spread intensity distribution h(k) of the incident beam is Gaussian distribution h(k;σ) here. FIG. 4 shows diffraction patterns (corresponding to the diffraction pattern of FIG. 1, and an upper right part is enlarged) when standard deviation σ is σ=0 (when there is no angle spread of incident beam), σ=1, and σ=2 and shows real images obtained by corresponding diffraction microscopy (see FIGS. 4A to 4C). Gaussian distribution h(k; σ) is provided by the following formula (4). Standard deviation σ is a parameter indicating the size of the angle spread of incident beam. The total number of counts is $10^7$, and the quantum noise is superimposed. Assuming that the camera length is L and the pixel size of detector 1 is p, the parameter of standard deviation σ can be converted to angle spread α of incident beam using a relationship α=(p/L) σ.

[Expression 4]

$$h(k;\sigma) = \frac{1}{\sqrt{2\pi}\,\sigma}\exp\left(-\frac{k^2}{2\sigma^2}\right) \qquad (4)$$

From the diffraction patterns shown on the left side of FIGS. 4A to 4C, it can be seen that the noise is large in an area with low intensity and that the intensity is gradually blurred with an increase in the angle spread of incident beam. From the real images obtained by the algorithm of FIG. 2 based on the diffraction patterns and shown on the right side of FIGS. 4A to 4C, there is almost no change is seen from the real image of FIG. 1 if σ=0, but the intensity is slightly different between the real images due to noise. When σ=1, there is large unevenness in the intensity of the points compared to the real image of FIG. 1. On the whole, the real image is blurred, and part of the real image can be hardly seen. When σ=2, the tendency as in the case of σ=1 is more prominent, and only part of the real image is reconfigured. The results indicate that the size of the reconfigured area is reduced with an increase in the angle spread of incident beam. This is a physically valid tendency because the angle spread of incident beam is a parameter for limiting the transverse coherence. The fact that the reconfigured image is thus reduced and blurred with an increase in the angle spread of incident beam is known as a problem of the diffraction microscopy.

Next, a principle of the present invention will be described.

If the angle spread of incident beam is a convolution as expressed by formula (2) without noise, diffraction intensity $I_0$ by the parallel incident beam without the angle spread of incident beam can be analytically obtained by inverse Fourier transform $F^{-1}$ as shown in formula (5).

[Expression 5]

$$I_0 = FT^{-1}\left\{\frac{FT\{I_{conv}\}}{FT\{h\}}\right\} \quad (5)$$

However, it is well known that it is difficult to obtain diffraction intensity $I_0$ by the parallel incident beam based on formula (5) if noise is superimposed on the measured diffraction pattern intensity (see NPL 10). Physical experiment cannot be performed without errors such as quantum noise and thermal noise of the detector.

In the field of diffraction microscopy, a specific methodology of reducing the influence of the angle spread of incident beam by deconvolution of a diffraction pattern convoluted by the angle spread of incident beam has not been proposed at all.

In the present invention, the influence of the angle spread of incident beam on diffractive imaging is reduced by deconvolution. Specifically, to reduce the influence of the angle spread of incident beam on diffractive imaging, (1) deconvolution is first applied to the convoluted diffraction pattern and then the pattern is used as the Fourier constraint to perform Fourier iterative phase retrieval, or (2) a sequential deconvolution method is incorporated into the Fourier iterative phase retrieval for the convoluted diffraction pattern.

Therefore, the present invention presents two methods (1) and (2) as specific methods of deconvolution for reducing the influence of the angle spread of incident beam. For the convenience, method (1) will be called invention method 1, and method (2) will be called invention method 2.

Figure 5A:
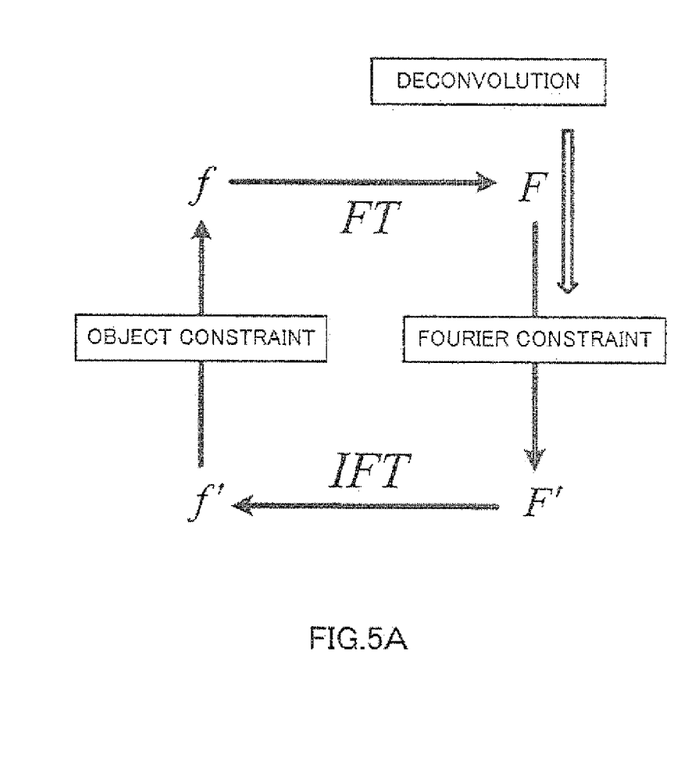
FIG. 5 is a diagram showing a principle (algorithm) of diffraction microscopy according to the present invention.
Figure 5B:
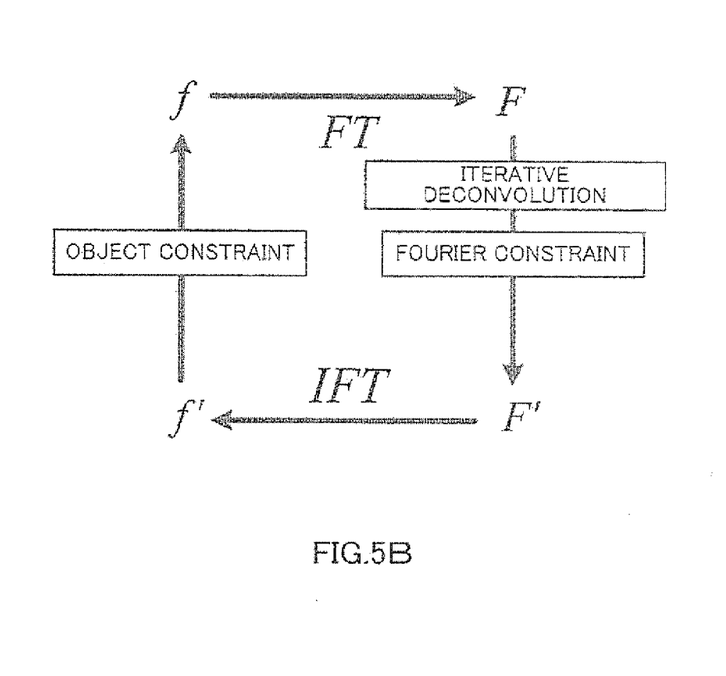

FIG. 5 is a diagram for describing the principle (algorithm) of the diffraction microscopy according to the present invention. Particularly, FIG. 5A corresponds to invention method 1, and FIG. 5B corresponds to invention method 2.

(1) As described, in invention method 1, deconvolution is first applied to the convoluted diffraction pattern, and then the pattern is used as the Fourier constraint to perform Fourier iterative phase retrieval of FIG. 2.

(2) In invention method 2, the sequential deconvolution method is incorporated into the Fourier iterative phase retrieval of FIG. 2 for the convoluted diffraction pattern.

A major difference between invention methods 1 and 2 is that while the deconvolution is applied to the convoluted diffraction pattern independently from the Fourier iterative phase retrieval in invention method 1, the deconvolution is incorporated into the Fourier iterative phase retrieval, and both are sequentially updated in invention method 2. Invention method 2 has an advantage that the constraint of the object is added to the deconvolution.

The method of deconvolution (specific formula) is not particularly limited in the present invention, and an arbitrary method can be adopted. The deconvolution for the angle spread of incident beam is not taken into account at all in the algorithm of FIG. 2. A major characteristic of the present invention is that the deconvolution is taken into account.

Hereinafter, specific algorithms of invention methods 1 and 2 will be described. To further clarify the features of the invention methods, the algorithm of FIG. 2 usually used in the diffraction microscopy (hereinafter, called an "algorithm of the conventional method") will be described first.

Based on intensity $I_{obs}$ of the measured diffraction pattern, amplitude $|F_{obs}|$ is expressed by formula (6), and two complex functions $f_n(r)$ and $F_n(k)$ shown in formulas (7) and (8) are abbreviated as in formulas (9) and (10), respectively. A formula obtained by replacing amplitude $|F_n|$ in formula (10) with amplitude $|F_{obs}|(=|F'_n|)$ is expressed by formula (11), and a formula after inverse Fourier transform of $F'_n$ of formula (11) is expressed by formula (12).

[Expression 6]

$$|F_{obs}| = \sqrt{I_{obs}} \quad (6)$$

[Expression 7]

$$f_n(r) = |f_n(r)|e^{i\phi_n(r)} \quad (7)$$

[Expression 8]

$$F_n(k) = |F_n(k)|e^{i\Phi_n(k)} \quad (8)$$

[Expression 9]

$$f_n = |f_n|e^{i\phi_n} \quad (9)$$

[Expression 10]

$$F_n = |F_n|e^{i\Phi_n} \quad (10)$$

[Expression 11]

$$F'_n = |F'_n|e^{i\Phi_n} \quad (11)$$

[Expression 12]

$$f'_n = |f'_n|e^{i\phi'_n} \quad (12)$$

The algorithm of the conventional method shown in FIG. 2 is formed by the following steps 1 to 6.

(Step 1) The object is set to $f_n$ (see formula (9)).

(Step 2) Fourier transform is applied to $f_n$, and the result is set to $F_n$ (see formula (10)).

(Step 3) Amplitude $|F_n|$ is replaced by amplitude $|F_{obs}|(=|F'_n|)$ obtained by measurement (Fourier constraint), and the result is set to $F'_n$ (see formula (11)).

(Step 4) Inverse Fourier transform is applied to $F'_n$, and the result is set to $f'_n$ (see formula (12)).

(Step 5) The object constraint is added to $f'_n$, and the result is set to $f_{n+1}$ shown in formula (13).

[Expression 13]

$$f_{n+1} = |f_{n+1}|e^{i\phi_{n+1}} \quad (13)$$

(Step 6) The process is finished if an evaluation value (for example, R factor shown in formula (14)) reaches a predetermined value ($R_{term}$), and the process returns to step 1 if the evaluation value does not reach the predetermined value.

[Expression 14]

$$R = \frac{\sum_k ||F(k)| - |F_{obs}(k)||}{\sum_k |F_{obs}(k)|} \quad (14)$$

Next, an algorithm of invention method 1 will be described.

In the algorithm of invention method 1, amplitude $|F_n|$ of the algorithm of the conventional method is replaced by $|F_{deconv}|(=|F'_n|)$ obtained by deconvolution of amplitude $|F_{obs}|$ calculated from measurement (Fourier constraint), and the result is set to $F'_n$ (see formula (11)).

More specifically, the algorithm of invention method 1 is formed by the following steps 1 to 6.

(Step 1) The object is set to $f_n$ (see formula (9)).

(Step 2) Fourier transform is applied to $f_n$, and the result is set to $F_n$ (see formula (10)).

(Step 3) Amplitude $|F_n|$ is replaced by $|F_{deconv}|$ ($=|F'_n|$) obtained by deconvolution of amplitude $|F_{obs}|$ calculated from measurement (Fourier constraint), and the result is set to $F'_n$ (see formula (11)).

(Step 4) Inverse Fourier transform is applied to $F'_n$, and the result is set to $f'_n$ (see formula (12)).

(Step 5) The object constraint is added to $f'_n$, and the result is set to $f_{n+1}$ shown in formula (13).

Next, an algorithm of invention method 2 will be described.

In the algorithm of invention method 2, amplitude $|F_n|$ of the algorithm of the conventional method is replaced by $|F_{deconv}|$ ($=|F'_n|$) obtained by sequential deconvolution (Fourier constraint), and the result is set to $F'_n$ (see formula (11)).

More specifically, the algorithm of invention method 2 is formed by the following steps 1 to 6.

(Step 1) The object is set to $f_n$ (see formula (9)).

(Step 2) Fourier transform is applied to $f_n$, and the result is set to $F_n$ (see formula (10)).

(Step 3) Amplitude $|F_n|$ is replaced by $|F_{deconv}|$ ($=|F'_n|$) obtained by sequential deconvolution (Fourier constraint), and the result is set to $F'_n$ (see formula (11)).

(Step 4) Inverse Fourier transform is applied to $F'_n$, and the result is set to $f'_n$ (see formula (12)).

(Step 5) The object constraint is added to $f'_n$, and the result is set to $f_{n+1}$ shown in formula (13).

There can be a plurality of methods (specific formulas) of the deconvolution used in invention methods 1 and 2 (see NPL 10). In the present embodiment, a Richardson-Lucy (RL) algorithm is used as an example of the method of deconvolution. The RL algorithm is provided by the following formula (15). Here, "*" denotes convolution, "t" denotes the number of iterations, and "h-bar" denotes a conjugate function of h.

[Expression 15]

$$I_{deconv}(t+1) = I_{deconv}(t) \frac{I_{noise}}{I_{deconv}(t) * h} * \bar{h} \qquad (15)$$

In formula (15), $|F_{deconv}(t)|$ and $|F_{obs}|$ are expressed by formulas (16) and (17), respectively. Therefore, in invention method 1, $|F_{deconv}(t)|$ is converted to $|F_{deconv}|$ after sufficient convergence by the RL algorithm of formula (15). In invention method 2, $I_{deconv}(t)$ on the right side of formula (15) is set to $|F_n|^2$ to obtain the left side, and $|F_{deconv}|$ is expressed by formula (18).

[Expression 16]

$$|F_{deconv}(t)| = \sqrt{I_{deconv}(t)} \qquad (16)$$

[Expression 17]

$$|F_{obs}| = \sqrt{I_{noise}} \qquad (17)$$

[Expression 18]

$$|F_{deconv}| = \sqrt{I_{deconv}(t+1)} \qquad (18)$$

The formula of deconvolution used in invention methods 1 and 2 is not limited to the RL algorithm shown in formula (15), and an arbitrary formula of deconvolution can be adopted.

Next, effects of the invention methods will be described.

As described, there are a plurality of methods for the deconvolution. An example of using the RL algorithm as one of the sequential deconvolutions in invention method 2 will be illustrated here.

FIG. 6 is a diagram showing an example of a process of convergence of deconvolution in invention method 2. The diffraction pattern of FIG. 4B (when σ=1) is used here to illustrate an image reconfiguration process when formula (15) is incorporated into the Fourier iterative phase retrieval shown in FIG. 5B. A graph of FIG. 6A shows the R factor quantitatively indicating the degree of convergence relative to the iterations. As described, the R factor is provided by formula (14). In the example shown in FIG. 6, HIO is applied up to 5000 iterations, and ER is applied after that and up to 10000 iterations.

Figure 6A:
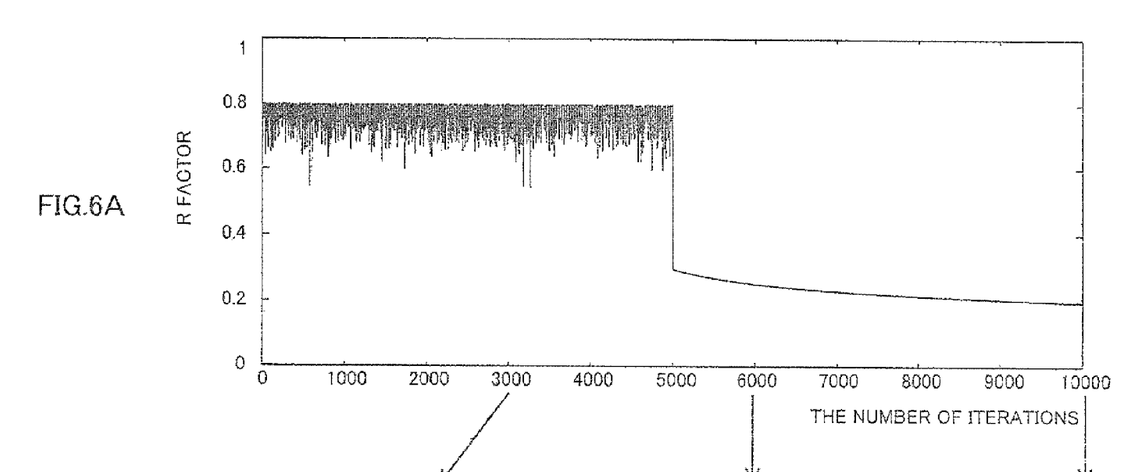
FIG. 6 is a diagram showing an example of a process of convergence of deconvolution in the diffraction microscopy according to the present invention.
Figure 6B:
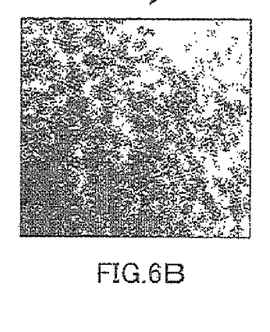
Figure 6C:
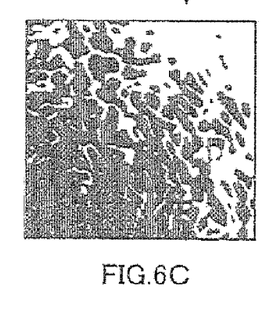
Figure 6D:
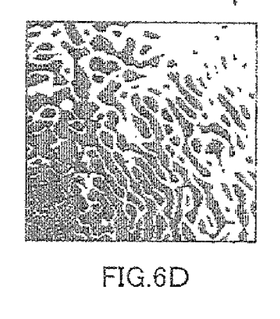

As shown in FIG. 6A, the R factor is substantially constant up to 5000 iterations. The R factor suddenly decreases just after the switch to ER, and then the R factor further decreases, although gradually. FIGS. 6B, 6C, and 6D show diffraction patterns at 3000 iterations, 6000 iterations, and 1000 iterations, respectively, as an example of the retrieval process. It can be seen from the diffraction patterns along with the advance of the iterations, the noise is reduced from blurred intensity with superimposed noise, and sharp interference fringes with sharp contrast specific to diffraction is clearly retrieved.

Figure 7A:
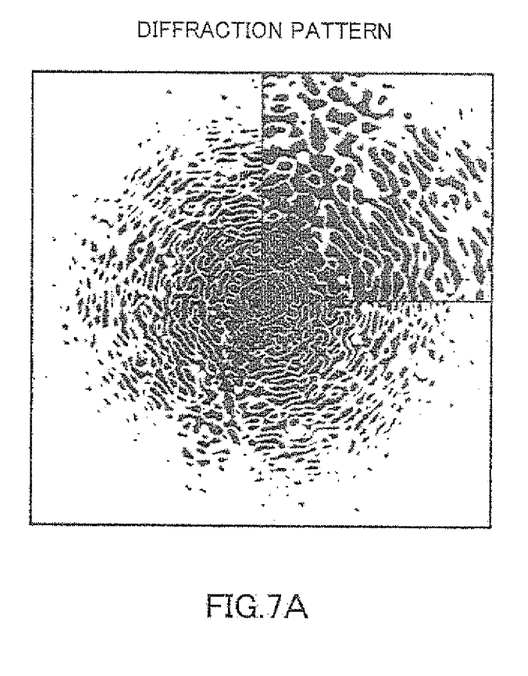
FIG. 7 is a diagram showing an example of an effect of the diffraction microscopy according to the present invention.
Figure 7B:
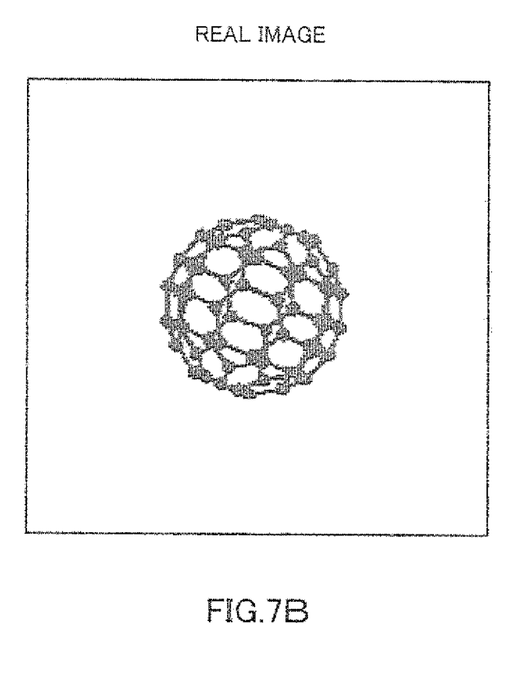

FIG. 7 is a diagram showing a diffraction pattern of the 10000th iteration in FIG. 6 and a corresponding real image (see FIG. 7B). Compared to the ideal case of FIG. 1 without the angle spread of incident beam, it can be seen that the diffraction pattern indicates substantially equivalent intensity (see FIG. 7A) and that although the contrast is slightly low in the real image, a satisfactory effect is attained compared to the real image of FIG. 4B (when σ=1) using the convoluted diffraction pattern as it is.

Hereinafter, an example of application to a specific apparatus will be described.

A diffraction pattern measurement apparatus and a computer are main constituent elements for measuring the diffraction pattern by experiment and carrying out the diffraction microscopy to obtain a real image by digital processing of a computer based on the diffraction pattern. Algorithms for carrying out the diffraction microscopy according to the present invention (for example, the algorithms of invention methods 1 and 2) are stored as programs in a predetermined storage device and are executed by the computer. Hereinafter, an example of application to an electron diffraction microscope will be described as an example of application of the diffraction microscopy according to the present invention. The electron diffraction microscope is an electron microscope that can measure the diffraction pattern without using an objective lens for image formation, while utilizing the performance of a conventional electron microscope. It is obvious that the example of application of the diffraction microscopy according to the present invention is not limited to the electron diffraction microscope.

Figure 8:
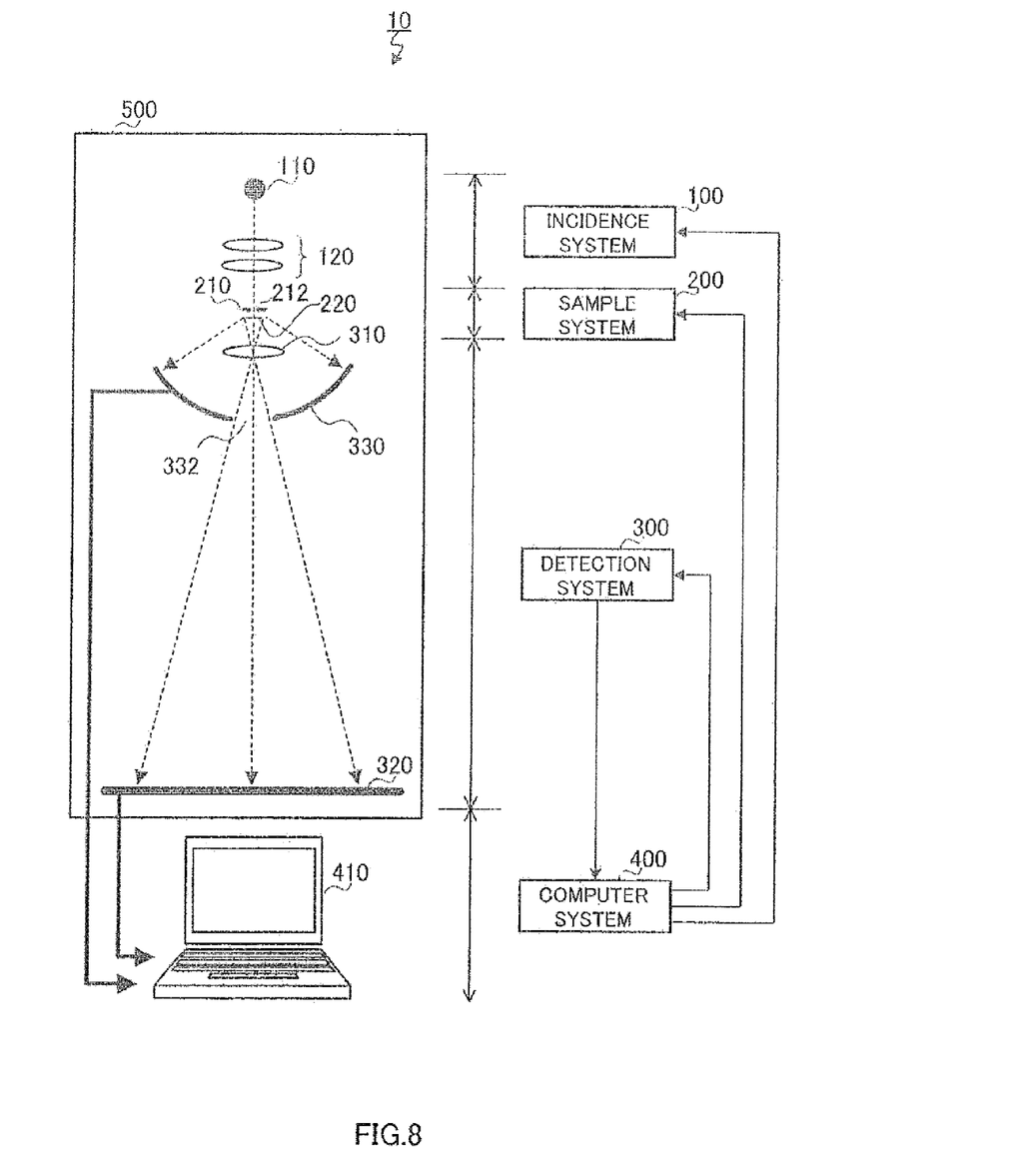
FIG. 8 is a block diagram showing an example of a hardware configuration of an electron diffraction microscope to which the diffraction microscopy according to the present invention is applied.

FIG. 8 is a block diagram showing an example of a hardware configuration of the electron diffraction microscope to which the diffraction microscopy according to the present invention is applied. Broadly speaking, although hardware and software are generally necessary to reconfigure the real image, FIG. 8 illustrates only the hardware of the electron diffraction microscope.

The hardware of electron diffraction microscope 10 shown in FIG. 8 is roughly divided into incidence system 100, sample system 200, detection system 300, and computer system 400. Incidence system 100, sample system 200, and detection system 300 are stored in vacuum case 500.

Incidence system 100 has a function of radiating a parallel electron beam on a sample and includes electron source 110 that generates the electron beam and lens system 120 for parallel radiation. Parallel radiation lens system 120 is formed by an electromagnetic lens. The electron beam generated by electron source 110 is converted by parallel radiation lens system 120 to a parallel electron beam, and the beam is radiated on sample system 200.

Sample system 200 has a function of fixing the sample and controlling the environment of the sample and includes support slit 210 and sample 220. Support slit 210 includes hole 212 at the center and is arranged in front of sample 220 relative to the radiation direction of the electron beam. Support slit 210 can add "phase" as an object constraint of the real space. More specifically, the intensity distribution and the phase distribution of support slit 210 are provided as object constraints in the Fourier iterative phase retrieval. Sample 220 is mounted on a sample stage not shown.

The "support" here denotes an area including the sample (observation area). The "support slit" includes two areas: an area including the sample; and an area other than the area. The former is a target image (image obtained by the diffraction microscopy), and the latter is an area in which the amplitude is set to zero as the object constraint.

Detection system 300 has a function of measuring the intensity of the diffraction pattern from the sample and includes objective lens 310, coarse detector 320, and fine detector 330. Fine detector 330 (for example, Ewald's sphere detector) includes hole 332 at the center (two-dimensional detector with center hole). Therefore, detection system 300 includes a coarse system and a fine system in this application example. The coarse system is a detection system for obtaining an image with relatively low spatial resolution by physical objective lens (objective lens that can be electrically turned on and off) 310. The fine system is a detection system for obtaining higher spatial resolution by the Fourier iterative phase retrieval using the intensity of the diffraction pattern, without using the physical objective lens. Objective lens 310 and coarse detector 320 are included in the coarse system, and fine detector 330 is included in the fine system. The installation of both the coarse system and the fine system allows using the real space image with low resolution, which is obtained by the coarse system, as a constraint of the phase retrieval of the fine system, and a high-resolution image can be obtained. Objective lens 310 is formed by an electromagnetic lens, and a magnifying lens system, such as an intermediate lens and a projection lens, is not illustrated in FIG. 8. The coarse detector and the fine detector can be integrated and used depending on the configuration.

Computer system 400 has a function of reconfiguring the image of the object using the Fourier iterative phase retrieval based on the intensity of the diffraction pattern measured by detection system 300 and is formed by computer 410. Coarse detector 320 and fine detector 330 of detection system 300 are connected to computer 410. A processing result of computer system 400 is fed back to incidence system 100, sample system 200, and detection system 300.

Although not shown, computer 410 includes a CPU that executes programs (algorithms), a storage device (such as a ROM, a RAM, and a hard disk) that stores the programs, a display that displays a processing result, and the like. The algorithms of invention methods 1 and 2 are stored as programs in the storage device included in computer 410 or in a computer-readable storage medium (such as a CD-ROM and a DVD) that can be connected to computer 410.

In electron diffraction microscope 10, an initial image and a support area can be obtained by the coarse system, and experiment data can be directly incorporated into an algorithm as an important object constraint of the diffraction microscopy. This indicates a specific example of materialization of the diffraction microscopy as an electron microscope. Therefore, complementary use of observation of a rough image (coarse image) by a conventionally attained method and observation of a detailed image (fine image) by the diffraction microscopy to obtain higher resolution is possible. The use of the diffraction microscopy according to the present invention (for example, algorithms of invention methods 1 and 2) as the diffraction microscopy can realize high resolution that is not conventionally attained, while reducing the influence of the angle spread of incidence.

The entire disclosure of the specification, the drawings, and the abstract included in Japanese Patent Application No. 2010-015698, filed Jan. 27, 2010, is hereby incorporated by reference.

Industrial Applicability

The diffraction microscopy according to the present invention can attain an advantageous effect of reducing the influence of the angle spread of incident beam, and for example, the diffraction microscopy can be widely applied to an electron microscope, a microscope using X-ray and light, and other microscopes using waves.

REFERENCE SIGNS LIST 1 detector
10 electron diffraction microscope
100 incidence system
110 electron source
120 parallel radiation lens system
200 sample system
210 support slit
212, 332 holes
220 sample
300 detection system
310 objective lens
320 coarse detector
330 fine detector
400 computer system
410 computer
500 vacuum case

The invention claimed is:

1. A diffraction microscopy method that radiates a beam on a sample, measures an intensity of a diffraction pattern from the sample, and uses a Fourier iterative phase retrieval based on the measured intensity of the diffraction pattern to reconfigure an image of an object,
wherein deconvolution is incorporated into the Fourier iterative phase retrieval for a diffraction pattern convoluted by an angle spread of incident beam, and both are sequentially updated.

2. A diffraction microscopy method that radiates a beam on a sample, measures an intensity of a diffraction pattern from the sample, and uses a Fourier iterative phase retrieval based on the measured intensity of the diffraction pattern to reconfigure an image of an object, comprising:
a first step of denoting the object by a predetermined first complex function $f_n$;
a second step of applying a Fourier transform to the first complex function $f_n$ to obtain a second complex function $F_n$;
a third step of sequentially deconvoluting an amplitude $|F_{obs}|$ expressed based on the measured intensity of the diffraction pattern, and replacing, as a Fourier constraint, an amplitude $|F_n|$ of the second complex function $F_n$ by a result $|F_{deconv}|$ obtained by the sequential deconvolution to obtain a third complex function $F'_n$;

a fourth step of applying an inverse Fourier transform to the third complex function $F'_n$ to obtain a fourth complex function $f'_n$; and a fifth step of adding an object constraint to the fourth complex function $f'_n$ to obtain an incremented first complex function $f_{n+1}$.

* * * * *